(12) United States Patent
Fitoussi et al.

(10) Patent No.: US 6,332,633 B1
(45) Date of Patent: Dec. 25, 2001

(54) LUER-TYPE CONNECTOR

(75) Inventors: Gilles Fitoussi, M.P. Merom Hagalil; Elisha Amir, Moshav Livnim, both of (IL)

(73) Assignee: Elcam Plastic Kibbutz Bar-Am, Merom Hagalil (IL)

( * ) Notice: Subject to any disclaimer, the term of this patent is extended or adjusted under 35 U.S.C. 154(b) by 0 days.

(21) Appl. No.: 09/460,990

(22) Filed: Dec. 15, 1999

(51) Int. Cl.⁷ .................................................... F16L 25/00
(52) U.S. Cl. ............................ 285/332; 285/354; 604/285
(58) Field of Search .............................. 285/332, 332.1, 285/354, 384–388, 247; 604/283

(56) References Cited

U.S. PATENT DOCUMENTS

| | | |
|---|---|---|
| 4,296,949 | 10/1981 | Muetterties et al. |
| 4,452,473 | 6/1984 | Ruschke . |
| 4,639,019 | 1/1987 | Mittleman . |
| 5,047,021 | 9/1991 | Utterberg . |
| 5,303,964 | 4/1994 | Yi . |
| 5,620,427 | 4/1997 | Werschmidt et al. . |
| 5,651,776 * | 7/1997 | Appling et al. .................. 285/332 X |
| 5,702,374 | 12/1997 | Johnson . |
| 5,894,373 * | 11/1999 | Fitoussi et al. ........................ 285/92 |

* cited by examiner

Primary Examiner—Teri Pham Luu
(74) Attorney, Agent, or Firm—Oliff & Berridge, PLC

(57) ABSTRACT

A luer-type connector comprising a male-component formed with a locking nozzle having a coaxially extending nozzle lumen, and a locking collar rotatable over said nozzle. The locking collar has a rear end and is formed with an internal thread for screw coupling with a corresponding thread of a radially extending annular lug of a mating female-component of the connector. The nozzle is formed with a ridge having a radially extending abutting wall surface facing the rear end of the locking collar and a peripheral surface extending forward from the abutting wall. An annular rim behind the abutting wall has a first diameter. An annular notch intermediate the abutting wall and the annular rim has a second diameter lesser than that of the first diameter. The locking collar is formed with a radially extending wall surface engageable with the abutting wall surface of the ridge. And an annular bulge behind the radial wall surface has a third diameter lesser than the first diameter. The annular bulge has an axial length lesser than an axial length of the annular notch and at least one locking surface of the locking collar having a diameter for interference fit with the corresponding peripheral surface and the annular rim of the nozzle.

9 Claims, 3 Drawing Sheets

LUER-TYPE CONNECTOR

FIELD OF THE INVENTION

This invention generally relates to luer-type connectors, and more specifically it is concerned with an improved male component of such connectors, which is fitted with a locking collar, the latter at times referred to also as a "hub".

BACKGROUND OF THE INVENTION

In a variety of medical products it is required to provide fast connecting means for connecting fluid transferring tubes to one another, for connecting tubes to branching devices and to different medical devices, as well as to a variety of flow control valves, etc.

For these and many other purposes, a variety of luer-type connectors are commonly utilized, which connectors provide on the one hand fast connecting and disconnecting, and on the other hand, provide reasonable reliability and security which is a critical requirement of such connectors to prevent un-intentional disconnection between the components, which under certain circumstances may be fatal for the patient or for the medical staff which may be exposed to contaminated body fluids. Still another problem which may occur in a connector non-tightly coupled is entry of air into the system which may be fatal.

Luer-type connectors are thus commonly in use. Various designs of luer-type connectors are available in which a tapered nozzle of a male-component is dimensioned to snugly, frictionally fit into a tapered socket of a female-component of the fitting, with a collar member rotatably retained over the male component and adapted for screw coupling with an annular threaded flanged portion of the female-component.

A variety of luer-type connectors are available and special consideration has been given to increased connecting force which at times may be required, e.g. to facilitate high pressure fluid flow through the connection and to prevent ingress of air into the system or, for extra precaution to prevent leakage of high risk fluids such as contaminated body fluids. However, excessive rotational force applied to the collar may eventually lead to disengagement of the collar from the male-component, entailing de-coupling of the connection which may result in a hazardous outcome.

In particular, the problem of disengagement of the collar from the male-component may occur while transferring fatty solutions which have a lubricating effect on the coupling, or even in case of unintentional excessive force applied to the collar, e.g. in case of stress of the medical staff. Evenmore, silicone oil is often applied at the zone of the selecting valve of such connectors.

Several attempts have been made to prevent unintentional disengagement of the rotatable collar from the male component. Such U.S. Pat. Nos. are for example: 4,296,949; 4,452,473; 4,639,019; 5,047,021; 5,303,964; 5,620,427; and 5,702,374.

It is an object of the present invention to provide a luer-type connector in of the aforementioned type with an improved male-component wherein locking of the male and female components is improved.

SUMMARY OF THE INVENTION

According to the present invention there is provided a A luer-type connector comprising a male-component formed with a locking nozzle having a coaxially extending nozzle lumen, and a locking collar rotatable over said nozzle, said locking collar having a rear end and is formed with an internal thread for screw coupling with a corresponding thread of a radially extending annular lug of a mating female-component of the connector; the nozzle being formed with a ridge having a radially extending abutting wall surface facing the rear end of the locking collar and a peripheral surface extending forward from the abutting wall; an annular rim behind said abutting wall, the rim having a first diameter; and an annular notch intermediate the abutting wall and the annular rim, said annular notch having a second diameter lesser than that of the first diameter; the locking collar being formed with a radially extending wall surface engageable with the abutting wall surface of the ridge for restricting forward axial displacement of the locking collar with respect to the nozzle; and an annular bulge behind said radial wall surface having a third diameter lesser than said first diameter, said annular bulge having an axial length lesser than an axial length of the annular notch; and at least one locking surface of the locking collar having a diameter for interference fit with the corresponding peripheral surface and the annular rim of the nozzle.

The arrangement of the invention is such that there is provided a definite locking position and wherein unlocking thereof is unlikely to occur unintentionally.

Preferably, the third diameter of the annular bulge is greater than the second diameter of the annular notch of the nozzle.

Still preferably, the locking collar is formed with a front locking surface forward of said radially extending wall surface for interference locking engagement with the peripheral surface of the nozzle. Alternatively or in combination, the locking collar is formed with a rear locking surface backward of the annular bulge for locking engagement with the annular rim of the nozzle.

By a preferred design, the third diameter of the annular bulge is lesser than the second diameter of the annular notch of the nozzle, for constituting interference fit therebetween.

According to a most preferred embodiment of the invention, the peripheral surface, annular notch and annular rim of the nozzle and the annular bulge and the at rear and front locking surfaces of the locking collar, are cylindrical.

In order to facilitate locking and unlocking of the locking collar with the female-component of the connector, the annular rim of the nozzle has chamfered front and rear edges.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1A:
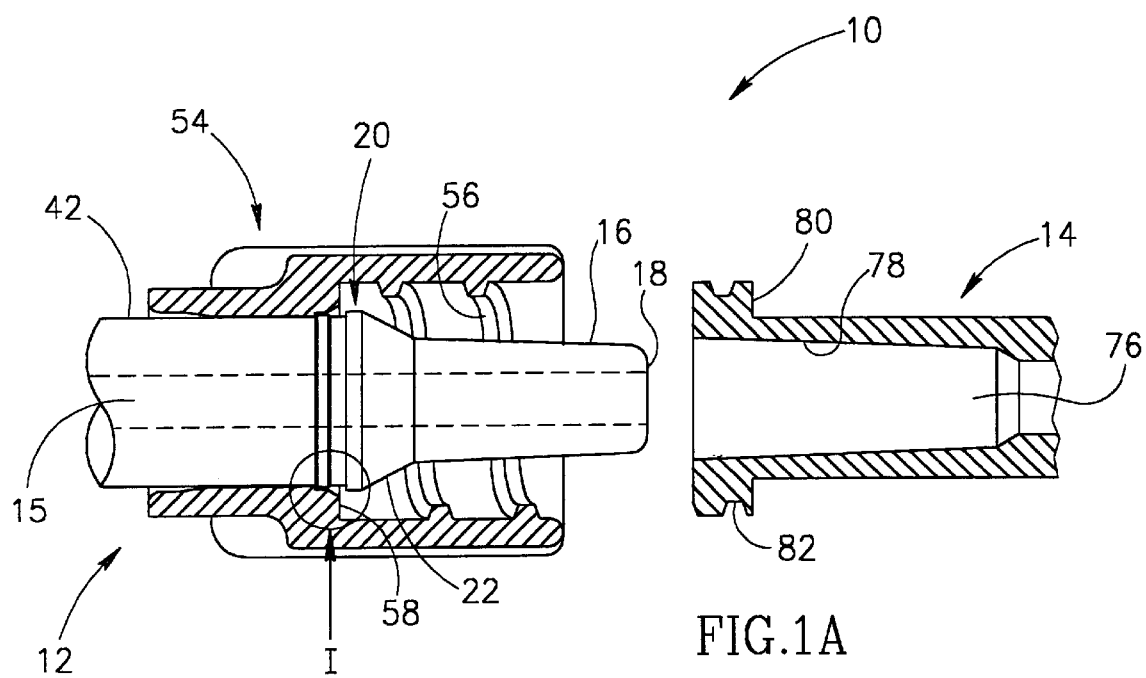
FIG. 1A is an axial section through a connector according to the present invention, the female-component being disengaged from the male-component.

FIG. 1A illustrates a luer-type connector generally designated 10 consisting of a male-component 12 and a female-component 14 and is formed with a co-axial lumen 15. Male-component 12 comprises a nozzle portion 16 tapering towards its front end 18. As can better be seen in FIG. 1B, at a rear end of nozzle 16 there is a ridge portion 20 consisting of a conical portion 22 tapering forwardly and a flat peripheral portion 24 being essentially cylindrical and terminating at an essentially radial abutting wall surface 26.

An annular rim 30 is formed rearward of said ridge portion 20 and has a first diameter D1. In the present embodiment the rim 30 is formed with rear and front chamfered edges 34 and 36, respectively.

An annular notch 40 is formed intermediate the abutting wall 26 and annular rim 30, and has a second diameter D2 being lesser than the first diameter D1 (D1>D2). In the depicted embodiment., the diameter D2 of the annular notch 40 is also lesser then the diameter of the cylindrical portion 42 at a rear end of the male-component 12.

A locking collar 54 is rotatably mounted over the male component 12. The locking collar 54 is formed with an internal threading 56 (FIG. 1A) and as can best be seen in the enlarged view of FIG. 1B, it is formed with a radially extending wall surface 58, being adapted for abutting engagement with wall surface 26 of the male component as will become apparent hereinafter.

Locking collar 54 is also formed with an annular bulge 64 extending rearwards from the radial wall 58 and having a third diameter D3 lesser than the first diameter D1. The axial length (width) of bulge 64 is lesser than the axial length (width) of the annular notch 40.

Figure 1B:
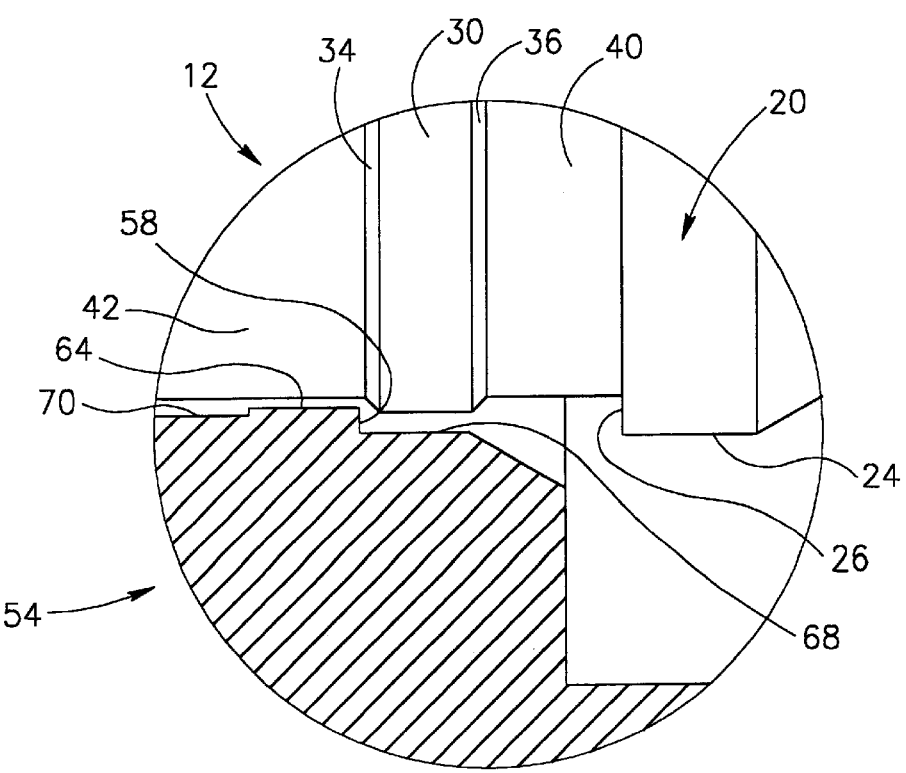
FIG. 1B is an enlargement of portion marked I in FIG. 1A.

As seen in the enlarged view of FIG. 1B, a front cylindrical locking surface 68 extends forward from the radial wall 58, and a rear cylindrical locking surface 70 extends rearwards of said annular bulge 64 and has a larger diameter than that of bulge 64.

The arrangement is such the diameters of the front and rear locking surfaces 68 and 70, of the locking collar 54, are smaller than the corresponding diameters of the cylindrical portion 42 and the peripheral portion 24, respectively, of the male-component 12, so as to ensured interference locking engagement therebetween, as will become apparent herein after with reference to FIGS. 2 and 3.

As seen in FIG. 1A, female-component 14 of the luer-type connector 10 has a lumen 76 with tapered walls 78 for frictional engagement over tapering nozzle 16 of the male component 12. Female-component 14 has at its front end an annular lug 80 formed with a threading 82 corresponding with that of the internal threading 56 of locking collar 54, as known per se.

In the position illustrated in FIGS. 1A and 1B, the locking collar 54 is disposed in a rear-most position with respect to the male-component 12. In this position forward displacement of the locking collar 54 over the male-component 12 renders the radial wall 58 to encounter annular rim 30 and thus some force is required to facilitate overcoming this obstacle, to the position of FIGS. 2.

Figure 2A:
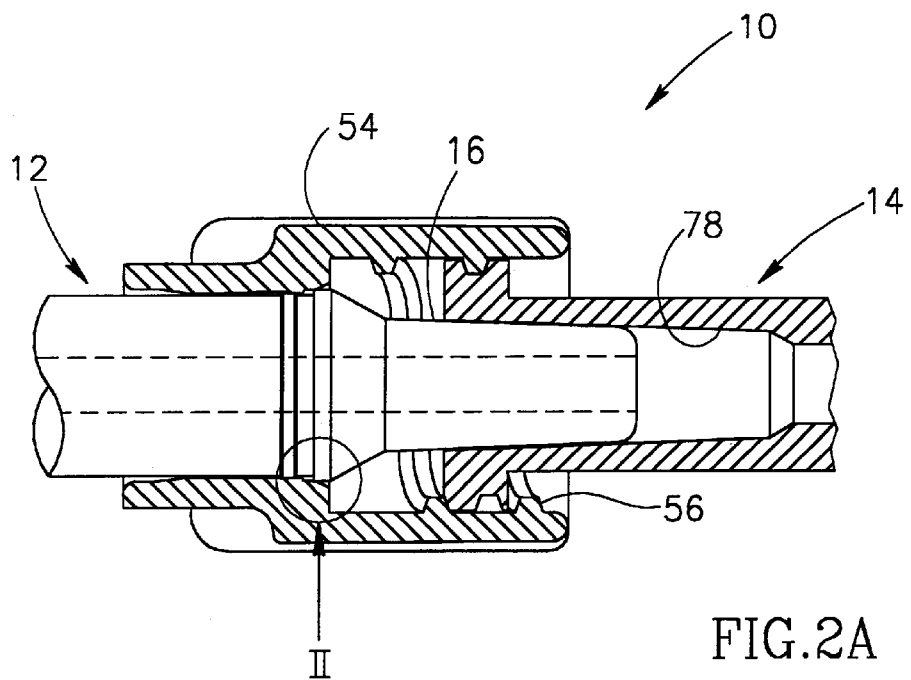
FIG. 2A is an axial section through a connector according to the present invention, the female-component being partially engaged with the male-component.
Figure 2B:
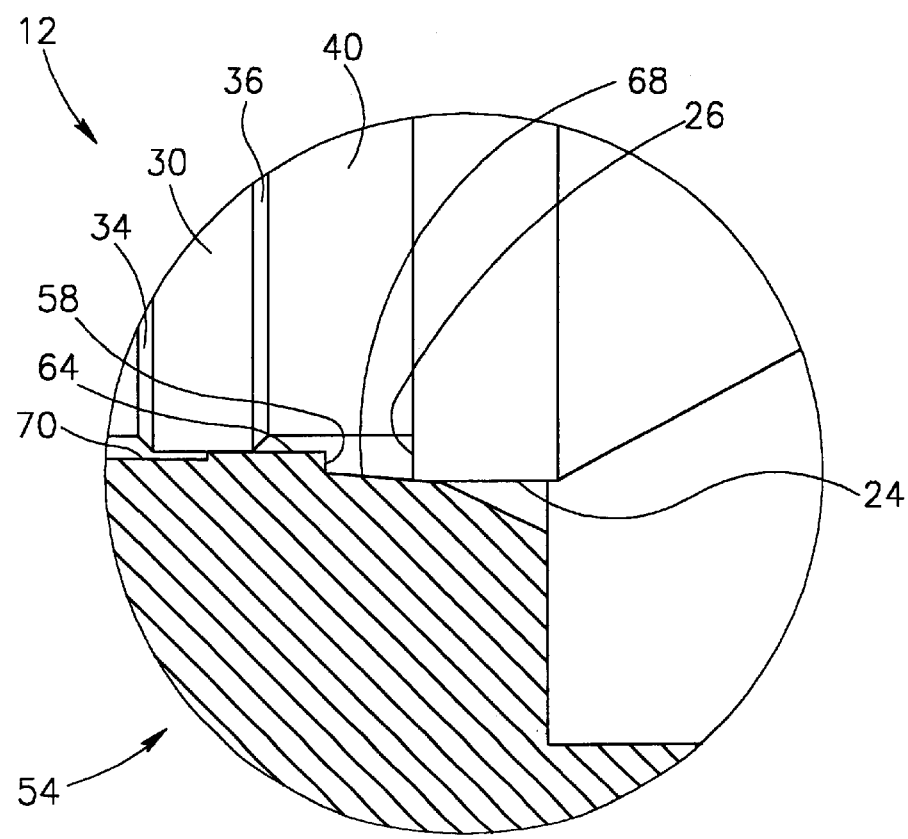
FIG. 2B is an enlargement of portion marked II in FIG. 2A.

Further attention is now directed to FIGS. 2A and 2B illustrating a first step in locking the connector, after the female-component 14 has been frictionally engaged over the nozzle 16 of the male-component 12. The male and female components are also partially locked with the locking collar 54 screw coupled with threading 82 of lug 80 of the female-component 14, wherein further rotation of the locking collar entails its further axial progress in a forward direction. In this position it is noted that the annular bulge 64 of the locking collar 54 partially overrides the annular rim 30 of the male-component 12.

It is also noted in FIGS. 2a and 2b that the front cylindrical portion 68 of the locking collar 54 has ascended over the flat peripheral portion 24 of the male-component 12. As already mentioned above, the diameters of these corresponding surfaces are designed so as to ensure interference engagement therebetween, and accordingly, the locking force increases as the two surfaces engage one another. However forward displacement of the locking collar 54 is restricted upon encountering of the respective radial wall portions 26 and 58, as in the position of FIGS. 3a and 3b.

Figure 3A:
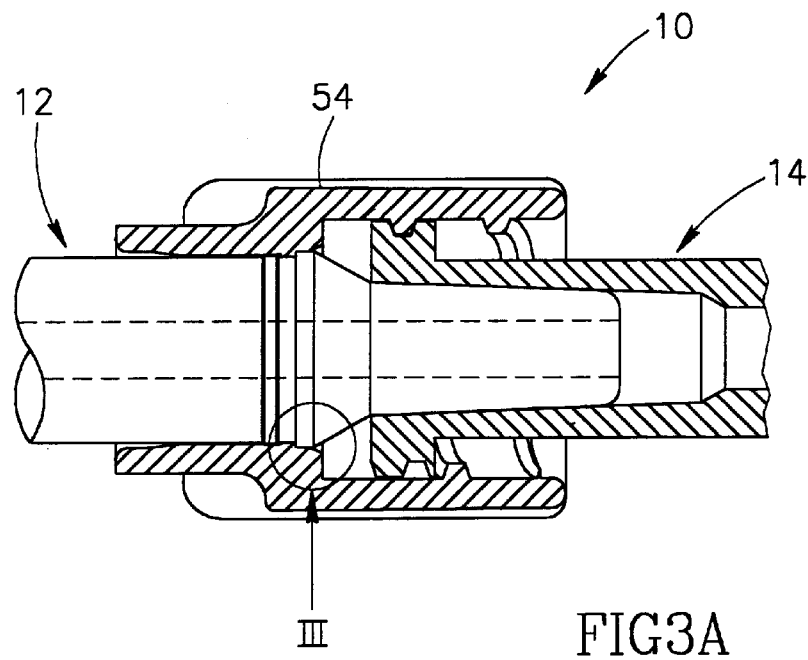
FIG. 3A is an axial section through a connector according to the present invention, the female-component being lockingly engaged with the male-component.
Figure 3B:
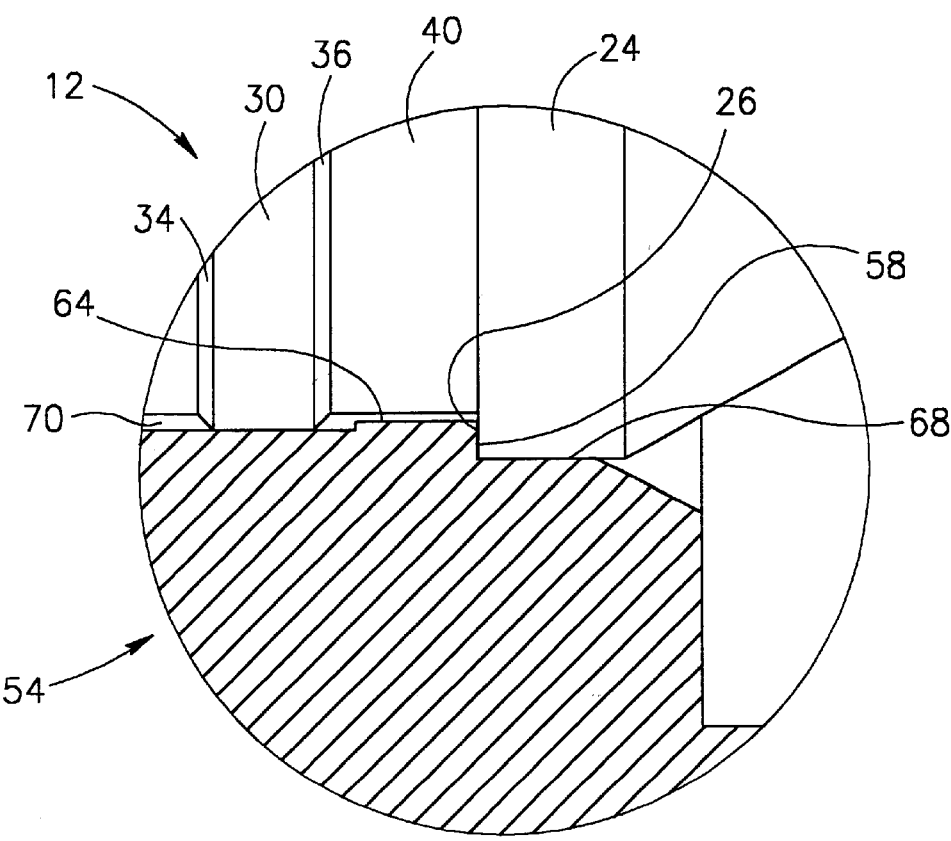
FIG. 3B is an enlargement of portion marked III in FIG. 3A.

Referring now to FIGS. 3A and 3B, the locking collar 54 has reached its most forward position wherein the radial wall portion 58 has encountered the respective radial wall portion 26 of the male-component 12. In this position the annular bulge 64 has descended from the annular rim 30 and it is now received within the annular notch 40. The annular bulge 64 does not engage the annular notch. However, the rear locking surface 70 is in interference locking engagement with the annular rim 30 of the male-component 12.

The arrangement of the invention is such that there is provided a definite locking position wherein the annular bulge is received within the annular notch and wherein unlocking thereof is unlikely to occur unintentionally as some significant force is required.

It will thus be appreciated that disconnecting the female-component of the connector is obtained in a reverse operation, namely, rotating the locking collar in an opposite direction such that the radial wall portions disengage, the annular bulge 64 ascends the annular rim 30 and than descends into its disengaged, unlocked position of FIGS. 1.

It will be appreciated by a skilled person that the design and structure of the luer-type connector in accordance with the present invention may be different than the specific design illustrated hereinabove. For example, rather than having both the rear and front locking surfaces be designed for interference engagement with the corresponding portions of the male-component, it would also be possible to have only either one of them lock engage.

In addition, other designs are possible to in which the annular bulge is designed so as to engage the annular notch also at interference engagement. Still a different modification would be forming one or more of the annular portions in a tapering shape with suitable design of the mating member for tight locking engagement therebetween.

What is claimed is:

1. A luer-type connector comprising a male-component formed with a locking nozzle having a coaxially extending nozzle lumen, and a locking collar rotatable over said nozzle, said locking collar having a rear end and is formed with an internal thread for screw coupling with a corresponding thread of a radially extending annular lug of a mating female-component of the connector; the nozzle being formed with a ridge having a radially extending abutting wall surface facing the rear end of the locking collar and a peripheral surface extending forward from the abutting wall; an annular rim behind said abutting wall, the rim having a first diameter; and an annular notch intermediate the abutting wall and the annular rim, said annular notch having a second diameter lesser than that of the first diameter; the locking collar being formed with a radially extending wall surface engageable with the abutting wall surface of the ridge for restricting forward axial displacement of the locking collar with respect to the nozzle, and an annular bulge behind said radial wall surface having a third diameter lesser than said first diameter, said annular bulge having an axial length lesser than an axial length of the annular notch; and at least one locking surface of the locking collar having a diameter for interference fit with the corresponding peripheral surface and the annular rim of the nozzle.

2. A connector according to claim 1, wherein the third diameter of the annular bulge is greater than the second diameter of the annular notch of the nozzle.

3. A connector according to claim 1, wherein the locking collar is formed with a front locking surface forward of said radially extending wall surface for interference locking engagement with the peripheral surface of the nozzle.

4. A connector according to claim 1, wherein the locking collar is formed with a rear locking surface backward of the annular bulge for locking engagement with the annular rim of the nozzle.

5. A connector according to claim 1, wherein the peripheral surface, annular notch and annular rim of the nozzle are cylindrical.

6. A connector according to claim 1, wherein the annular bulge and the at least one locking surface of the locking collar are cylindrical.

7. A connector according to claim 1, wherein the annular rim of the nozzle has a chamfered rear edge.

8. A connector according to claim 7, wherein the annular rim of the nozzle has a chamfered front edge.

9. A connector according to claim 1, wherein the annular bulge of the female component extends from an edge of the radial wall surface.

* * * * *